(12) United States Patent
Omori et al.

(10) Patent No.: US 9,187,374 B2
(45) Date of Patent: Nov. 17, 2015

(54) CERAMICS PASTE AND LAMINATED BODY

(71) Applicant: NGK INSULATORS, LTD., Nagoya (JP)

(72) Inventors: Takeshi Omori, Niwa-Gun (JP); Koichi Iwata, Kani (JP); Masahiro Abe, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 51 days.

(21) Appl. No.: 13/849,680

(22) Filed: Mar. 25, 2013

(65) Prior Publication Data
US 2013/0260983 A1 Oct. 3, 2013

(30) Foreign Application Priority Data

Mar. 28, 2012 (JP) ................................. 2012-073050
Feb. 21, 2013 (JP) ................................. 2013-031970

(51) Int. Cl.
C04B 35/10 (2006.01)
B32B 18/00 (2006.01)
(Continued)

(52) U.S. Cl.
CPC ................ *C04B 35/10* (2013.01); *B32B 18/00* (2013.01); *C04B 35/111* (2013.01); *C04B 35/14* (2013.01); *C04B 35/453* (2013.01); *C04B 35/46* (2013.01); *C04B 35/486* (2013.01); *C04B 35/6264* (2013.01); *C04B 35/6342* (2013.01); *C04B 35/6346* (2013.01); *C04B 35/63424* (2013.01); *C04B 35/63444* (2013.01); *C04B 35/63456* (2013.01); *C04B 35/63488* (2013.01);

(Continued)

(58) Field of Classification Search
CPC ........................................................ C04B 35/00
USPC ........................................................ 524/106
See application file for complete search history.

(56) References Cited

U.S. PATENT DOCUMENTS

| 4,680,154 | A | * | 7/1987 | Matsubara et al. ........... 264/639 |
| 2006/0280933 | A1 | * | 12/2006 | Kobayashi et al. ........... 428/325 |
| 2007/0166570 | A1 | | 7/2007 | Cutler et al. |
| 2008/0156644 | A1 | | 7/2008 | Suzuki et al. |
| 2012/0041123 | A1 | * | 2/2012 | Ootsuki et al. ................ 524/390 |

FOREIGN PATENT DOCUMENTS

EP 1 816 112 8/2007
JP 09-157033 A1 6/1997
(Continued)

OTHER PUBLICATIONS

European Search Report, European Patent Application No. 13160979.4, dated Oct. 17, 2013 (9 pages).
(Continued)

*Primary Examiner* — Ling Choi
*Assistant Examiner* — Lanee Reuther
(74) *Attorney, Agent, or Firm* — Burr & Brown, PLLC

(57) ABSTRACT

A NOx sensor 100 is produced by forming a stack with a ceramics paste including ceramic particles, a resin, a solvent, and one or more additives selected from additives of a first group having a first structure containing one or more selected from ether structures, urethane structures, hydroxy group-containing structures, ester structures, and acrylic structures and additives of a second group having any one or more structures of the additives of the first group and a second structure containing one or more selected from imidazoline structures, ethylenediamine structures, and amine structures. The ceramics paste contains any one of the additives of the first group and the second group and thus has an appropriate affinity for a cutting edge at the time of cutting a laminated body before the firing of the NOx sensor 100.

12 Claims, 4 Drawing Sheets

(51) Int. Cl.

| | |
|---|---|
| *C04B 35/111* | (2006.01) |
| *C04B 35/14* | (2006.01) |
| *C04B 35/453* | (2006.01) |
| *C04B 35/46* | (2006.01) |
| *C04B 35/486* | (2006.01) |
| *C04B 35/626* | (2006.01) |
| *C04B 35/634* | (2006.01) |
| *G01N 33/00* | (2006.01) |
| *C04B 37/00* | (2006.01) |

(52) U.S. Cl.
CPC .......... *C04B37/008* (2013.01); *G01N 33/0037* (2013.01); *C04B 2235/3217* (2013.01); *C04B 2235/3225* (2013.01); *C04B 2235/3418* (2013.01); *C04B 2235/5445* (2013.01); *C04B 2235/6025* (2013.01); *C04B 2235/6028* (2013.01); *C04B 2235/612* (2013.01); *C04B 2235/963* (2013.01); *C04B 2237/34* (2013.01); *C04B 2237/341* (2013.01); *C04B 2237/343* (2013.01); *C04B 2237/346* (2013.01); *C04B 2237/348* (2013.01); *C04B 2237/62* (2013.01); *C04B 2237/704* (2013.01)

(56) References Cited

FOREIGN PATENT DOCUMENTS

| | | |
|---|---|---|
| JP | 2000-103643 A1 | 4/2000 |
| JP | 2002-321980 A1 | 11/2002 |
| JP | 2002-321981 | 11/2002 |
| JP | 2002321981 A * | 11/2002 |
| JP | 2005-089200 A1 | 4/2005 |
| JP | 2005-247660 A1 | 9/2005 |
| JP | 2007-191387 A1 | 8/2007 |
| JP | 2008-164411 | 7/2008 |
| JP | 2011-082149 A1 | 4/2011 |
| JP | 2011-195436 A1 | 10/2011 |
| JP | 2013-067552 | 4/2013 |
| WO | 2013/035573 | 3/2013 |

OTHER PUBLICATIONS

Raeder, H. et al., "Tape Casting of Zirconia for Ion Conducting Membranes: A Study of Dispersants," Journal of the European Ceramic Socity, Elsevier Science Publishers, Barking, Essex, GB, vol. 13, No. 6., dated Jan. 1. 1994, (pp. 485-491) (7 pages).

* cited by examiner

CERAMICS PASTE AND LAMINATED BODY

CROSS-REFERENCE TO RELATED APPLICATIONS

The present application claims priority from Japanese Patent Application No. 2012-073050 filed on Mar. 28, 2012, and Japanese Patent Application No. 2013-031970 filed on Feb. 21, 2013, the entire contents of which are incorporated herein by reference.

BACKGROUND OF THE INVENTION

1. Field of the Invention

The present invention relates to a ceramics paste and a laminated body.

2. Description of the Related Art

Hitherto, a NOx sensor including a detection electrode containing a noble metal and a raw-material powder for a solid electrolyte layer has been reported, in which the impedance of a pump cell and the measurement sensitivity can be stabilized during the use of the NOx sensor (for example, see PTL 1).

CITATION LIST

[PTL 1] Japanese Unexamined Patent Application Publication No. 2008-164411

SUMMARY OF THE INVENTION

The NOx sensor is produced by mixing a stabilized zirconia powder, an organic binder, a plasticizer, and an organic solvent together to prepare a paste, forming the paste into green sheets by a doctor blade method or the like, stacking the green sheets to form a laminated body, and performing firing. In some cases, for example, a laminated body in which a plurality of NOx sensors are integrally stacked is formed, cut, and fired to produce the plural NOx sensors. When the laminated body is cut, a cut surface can be roughened, thereby causing a failure, such as the formation of a crack in the cut surface after firing.

The present invention has been accomplished in view of the problem. It is a main object of the present invention to provide a ceramics paste that forms an appropriate surface to further reduce the occurrence of a failure, and a laminated body.

The inventors have conducted intensive studies to achieve the forgoing main object and have found that the addition of a specific additive to a ceramics paste used to produce a laminated body results in an appropriate surface to further reduce the occurrence of a failure. This finding has led to the completion of the present invention.

That is, a ceramics paste of the present invention includes:
ceramic particles,
a resin,
a solvent, and
one or more additives selected from additives of a first group having a first structure containing one or more selected from ether structures, urethane structures, hydroxy group-containing structures, ester structures, and acrylic structures, and additives of a second group having any one or more structures of the additives of the first group and a second structure containing one or more selected from imidazoline structures, ethylenediamine structures, and amine structures.

A laminated body of the present invention is produced by the use of the foregoing ceramics paste. For example, the laminated body of the present invention is produced by, if necessary, forming a predetermined pattern on each green sheet with the ceramics paste or forming a cavity, and pressure-bonding the green sheets with each other to stack the sheets.

In the ceramics paste and the laminated body of the present invention, an appropriate surface can be provided, thereby further reducing the occurrence of a failure. The reason for this is unclear but is believed that when the laminated body produced by the use of the ceramics paste is cut, a functional group and so forth contained in any of the foregoing additives act to adjust the adhesion of a cut surface of the laminated body to a cutting edge to an appropriate state. It is thus speculated that, for example, the appropriate shape of the cut surface results in a further inhibition of the occurrence of cracking and so forth that can occur at the cut surface of the laminated body after cutting, thereby further reducing the occurrence of a failure.

DETAILED DESCRIPTION OF THE INVENTION

Figure 1:
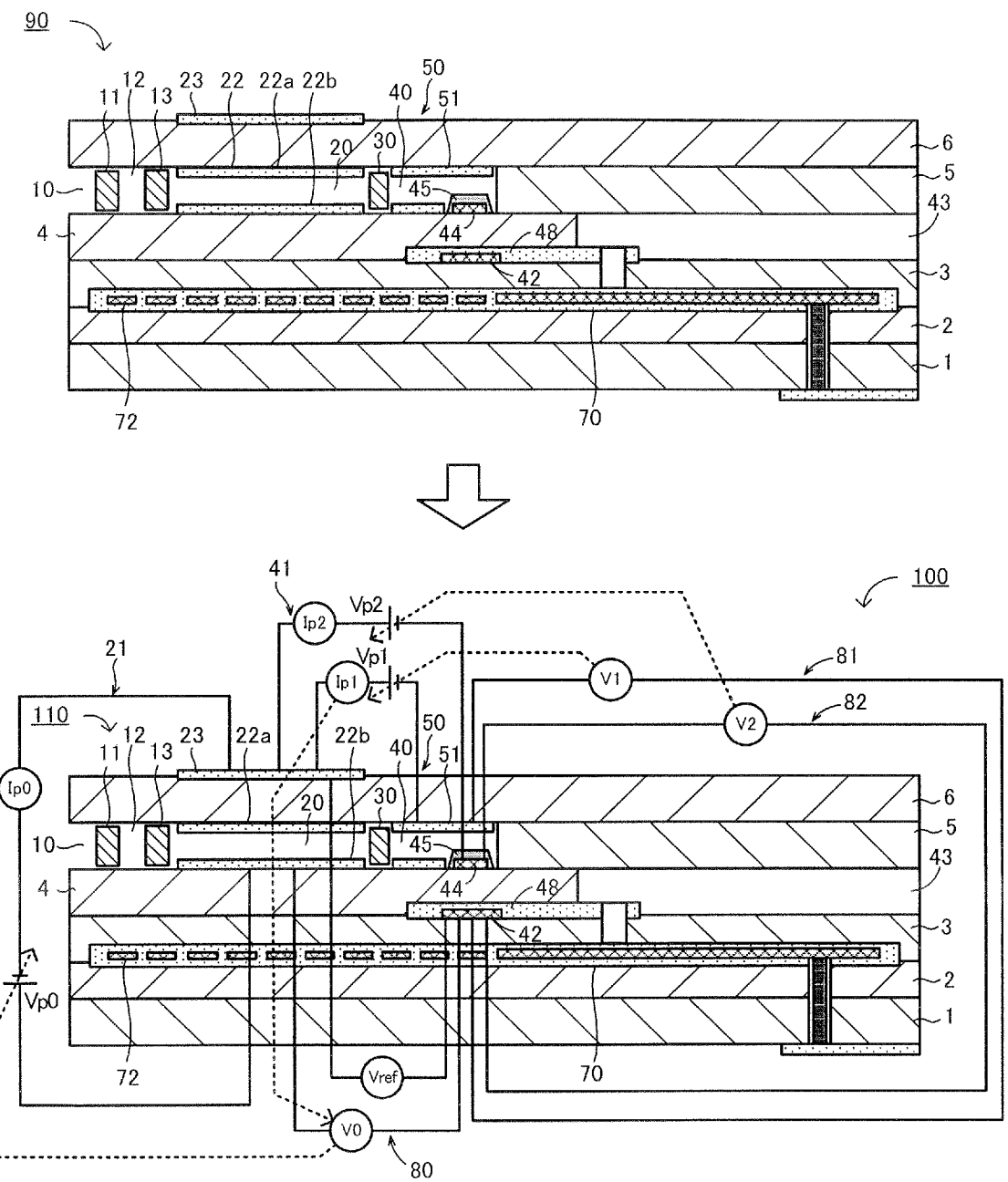
FIG. 1 is a schematic structural view illustrating a laminated body 90 and a NOx sensor 100.
Figure 2:
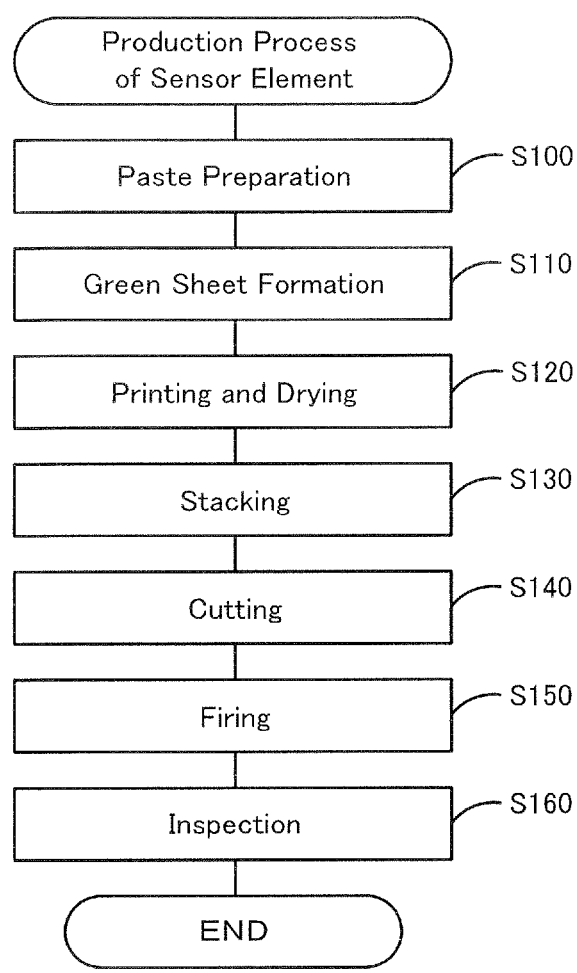
FIG. 2 is a flow chart illustrating a production process of a sensor element.

Embodiments of the present invention will be described below with reference to the drawings. FIG. 1 is a schematic structural view illustrating a laminated body 90 and a NOx sensor 100. FIG. 2 is a flow chart illustrating a production process of a sensor element. The laminated body 90 illustrated in FIG. 1 can be produced with a ceramics paste of the present invention. The ceramics paste of the present invention contains ceramic particles, a resin, a solvent, and a predetermined additive.

The ceramic particles may be composed of, for example, a metal oxide, a metal carbide, a metal nitride, or a metal composite compound or a mixture thereof. Specific examples of the metal oxide include $Al_2O_3$, $SiO_2$, $TiO_2$, $ZnO$, and $ZrO_2$. Among these, $ZrO_2$, in particular, Y-stabilized $ZrO_2$, and so forth are preferred. Examples of the metal carbide include SiC, $B_4C$, and $CaC_2$. Examples of the metal nitride include BN, $Si_3N_4$, and GaN. Examples of the metal composite compound include metal complex oxides, such as $Pb(Zr,Ti)O_3$, $NaNbO_3$, $LiNbO_3$, and $LiTaO_3$. The particle size of the ceramic particles may be appropriately selected, depending on a target laminated body. For example, $Al_2O_3$ preferably has an average particle size of 0.10 μm or more and 0.40 μm or less and more preferably 0.15 μm or more and 0.35 μm or less. For example, $ZrO_2$ preferably has an average particle size of 0.40 μm or more and 0.80 μm or less and more preferably 0.5 μm or more and 0.7 μm or less. Here, the "average particle size" indicates a median particle size (D50) measured by a laser diffraction/scattering particle size measurement. Regarding the amount of the ceramic particles contained, for example, the amount of $Al_2O_3$ contained is preferably 25% by mass or more and 60% by mass or less and more preferably 35% by mass or more and 55% by mass or less with respect to the total amount of the ceramics paste. The amount of $ZrO_2$ contained is preferably 40% by mass or more and 70% by mass or less and more preferably 55% by mass or more and 65% by mass or less with respect to the total amount of the ceramics paste.

The resin functions as a binder that solidifies the ceramic particles. Examples of the resin include butyral resins and poly(meth)acrylic ester resins. Among these, a butyral resin is preferred. The butyral resin may have a butyral resin structure. For example, as illustrated in formula (1), the butyral resin may also contain a butyral group, an acetyl group, and a hydroxy group in a predetermined ratio. The butyral resin may have a butyral content of, for example, 60 mol % or more and 75 mol % or less, an acetyl group content of 3 mol % or more and 10 mol % or less, and a hydroxy group content of 20 mol % or more and 40 mol % or less. For example, the butyral resin may have a low degree of polymerization, i.e. a molecular weight of less than $4 \times 10^4$, may have a medium degree of polymerization, i.e., a molecular weight of $4 \times 10^4$ or more and $1 \times 10^5$ or less, or a high degree of polymerization, i.e., a molecular weight of more than $1 \times 10^5$. In particular, a butyral resin having a low degree of polymerization is preferably used. For example, the butyral resin having a low degree of polymerization may have a transition temperature Tg in the range of 58° C. or higher and 68° C. or lower and a viscosity in the range of 8 mPa·s or more and 50 mPa·s or less. For example, the butyral resin having a medium degree of polymerization may have a transition temperature Tg in the range of 60° C. or higher and 68° C. or lower and a viscosity in the range of 60 mPa·s or more and 180 mPa·s or less. For example, the butyral resin having a high degree of polymerization may have a transition temperature Tg in the range of 65° C. or higher and 90° C. or lower and a viscosity in the range of 80 mPa·s or more and 200 mPa·s or less. The amount of the butyral resin contained is preferably in the range of 4% by mass or more and 15% by mass or less and more preferably 6% by mass or more and 11% by mass or less with respect to the total amount of the ceramics paste.

[Formula 1]

Formula (1)

Butyral Resin Structure

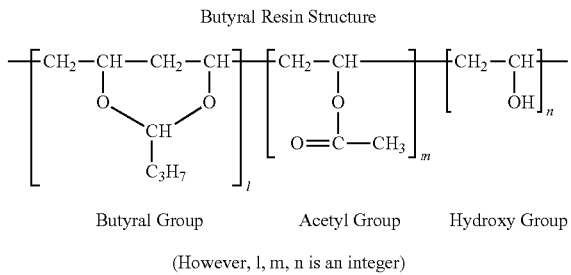

Butyral Group    Acetyl Group    Hydroxy Group (However, l, m, n is an integer)

The solvent is not particularly limited as long as it can be mixed with ceramic particles and a resin to form a paste, and may be a common organic solvent. For example, the solvent may be a monohydric alcohol having 6 to 12 carbon atoms, a cellosolve-based solvent, an ester bond-containing compound, or a compound having a terpineol structure. These compounds may be used alone or in combination of two or more as a mixture. Examples of the solvent include 2-ethylhexanoic acid, 2-ethylhexanol, 2-ethylhexyl acetate, and 2-ethylhexyl methacrylate. Examples of the terpineol compound include α-terpineol, β-terpineol, γ-terpineol, and dihydroterpineol. Among these, dihydroterpineol (also referred to as menthanol) illustrated in formula (2) is preferred. The amount of the solvent contained is preferably in the range of 22% by mass or more and 30% by mass or less and more preferably 24% by mass or more and 28% by mass or less with respect to the total amount of the ceramics paste.

[Formula 2]

Formula (2)

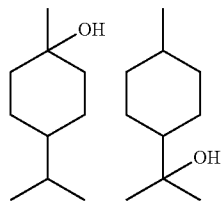

For example, the additive may serve as a lubricant during the cutting of a laminated body produced by using the ceramics paste in an adhesive layer for ceramics green sheets and stacking the sheets. The additive is one or more selected from additives of a first group having a first structure containing one or more selected from ether structures, urethane structures, hydroxy group-containing structures, ester structures, and acrylic structures; and additives of a second group having any one or more structures of the additives of the first group and a second structure containing one or more selected from imidazoline structures, ethylenediamine structures, and amine structures. The amount of the additive contained is preferably in the range of 0.1% by mass or more and 10.0% by mass or less and more preferably 0.5% by mass or more and 5.0% by mass or less with respect to the total amount of the ceramics paste. When the amount contained is 0.1% by mass or more, the additive can be more effective in providing a suitable cut surface of the ceramics green sheet. When the amount contained is 10.0% by mass or less, for example, failure, such as the formation of air bubbles, can be more inhibited during the use of the ceramics paste.

The additives of the first group each have the first structure containing one or more selected from ether structures, urethane structures, hydroxy group-containing structures, ester structures, and acrylic structures. Each of the additives of the first group may contain at least one selected from low-molecular-weight organic compounds containing functional groups with affinities for ceramic particles, high-molecular-weight copolymers containing functional groups with affinities for ceramic particles, block copolymers containing functional groups with affinities for ceramic particles, oligomers containing functional groups with affinities for ceramic particles, and phenol ethoxylate containing functional groups with affinities for ceramic particles. Specific examples thereof are described below. An example of the additives that contain low-molecular-weight organic compounds containing functional groups with affinities for ceramic particles is DISPERBYK-108 ("DISPERBYK" is a registered trademark, and the same applies hereinafter) available from BYK Japan K.K. Examples of the additives that contain high-molecular-weight copolymers containing functional groups with affinities for ceramic particles include DISPERBYK-162, DISPERBYK-164, DISPERBYK-182, and DISPERBYK-2050, which are available from BYK Japan K.K. Examples of the additives that contain block copolymers containing functional groups with affinities for ceramic particles include DISPERBYK-2155 and DISPERBYK-2164. Examples of the additives that contain phenol ethoxylate containing functional groups with affinities for ceramic particles include ADEKA TOL (registered trademark, the same APPENDIX A applies hereinafter) PC-6, ADEKA TOL PC-8, ADEKA TOL PC-10, and ADEKA TOL SP-12, which are available from ADEKA CORPORATION. In addition, an example of the additives that contain polyoxyalkylene ether is ADEKA NOL (registered trademark, the same applies hereinafter) B-4001.

In addition, examples of the additives of the first group include SN-Spers (registered trademark, the same applies hereinafter) 70 (nonionic surfactant), SN-Wet 366 (nonionic surfactant), and SN-Dispersant 9228 (ester-type nonionic surfactant), which are available from SAN NOPCO LTD. Furthermore, examples of the additives of the first group include TEGO (registered trademark, the same applies hereinafter) Dispers 610 (solution of a polymeric fatty acid derivative), TEGO Dispers 652 (fatty acid derivative), TEGO Dispers 670 (modified polyester), TEGO Dispers 685 (modified polyester), and TEGO Dispers 700 (solution of a fatty acid derivative), which are available from EVONIK INDUSTRIES.

The additives of the second group each have any one or more structures of the additives of the first group and the second structure containing one or more selected from imidazoline structures, ethylenediamine structures, and amine structures. That is, the additives of the second group each have one or two or more structures of the additives of the first group and one or two or more structures of the second structure. Each of the additives of the second group may contain at least one selected from compounds having alkenylimidazoline structures and polyoxyalkylene condensates of ethynediamine. Specific examples thereof are described below. An example of the compounds having alkenylimidazoline structures is DISPERBYK-109 available from BYK Japan K.K. Examples of the polyoxyalkylene condensates of ethynediamine include ADEKA NOL TR-702, ADEKA NOL TR-704, and ADEKA PLURONIC (registered trademark, the same applies hereinafter) TR-913R, which are available from ADEKA CORPORATION.

In addition, examples of the additives of the second group include NOPCO (registered trademark, the same applies hereinafter) 38-C (anionic activator) and NOPCO WET 50 (anionic activator), which are available from SAN NOPCO LTD. Furthermore, Examples of the additives of the second group include TEGO Dispers 630 (solution of a high-molecular-weight polycarboxylic acid and an amine derivative) and TEGO Dispers 662C (special cationic surfactant), which are available from EVONIK INDUSTRIES.

Examples of additives of a third group, which is not preferably used as an additive of the present invention, include additives each having any one or more structures of the first structure and the second structure and one or more selected from phosphate salts, sulfonates, carboxylates, alkylammonium salts, and acid group-containing compounds. Specific examples thereof include DISPERBYK-101 containing a salt of a long-chain polyaminoamide and a polar acidic ester, DISPERBYK-106 containing a salt of a polymer with an acidic group, DISPERBYK-140 containing an ammonium salt of an acidic polymer, DISPERBYK-145 containing a phosphate salt, and DISPERBYK-180 containing an alkylolamine salt of a copolymer with an acidic group, which are available from BYK Japan K.K.

In addition, examples of the additives of the third group include SN-Spers (amine salt of a polycarboxylic acid), SN-Dispersant 5027 (ammonium salt of a polycarboxylic acid, anionic, 20%), SN-Dispersant 5468 (ammonium salt of a polycarboxylic acid, anionic, 40%), Nopcosant RFA (ammonium salt of a polycarboxylic acid, anionic, 40%), and SN-Dispersant 5020 (ammonium salt of a polycarboxylic acid, anionic, 40%), which are available from SAN NOPCO LTD.

Furthermore, an example of the additives of the third group is TEGO Dispers 710 (butyl acetate/methoxypropyl acetate: urethane polymer) available from EVONIK INDUSTRIES.

The ceramics paste of the present invention may contain a plasticizer as an additional component. As the plasticizer, a common plasticizer may be used. For example, a phthalate with an ester moiety having 4 to 12 carbon atoms may be used.

The ceramics paste of the present invention may be formed on, for example, a green sheet containing ceramic particles. The thickness of the ceramics paste formed on the green sheet may be, for example, 1 µm or more, 10 µm or more, or 80 µm or more. A larger thickness is more likely to provide the effect of the ceramics paste of the present invention. As a method for forming the ceramics paste, for example, screen printing, gravure printing, or a doctor blade method may be employed. The green sheet may contain, for example, the ceramic particles and a butyral resin. As the ceramic particles, any of the foregoing ceramic particles may be used. Here, the butyral resin contained in the green sheet may be different from the butyral resin contained in the ceramics paste. In this case, for example, a mixed solvent in the ceramics paste dissolves the butyral resin in the ceramics paste but is less likely to dissolve the butyral resin in the green sheet. For example, the ceramics paste may contain a butyral resin having a low degree of polymerization, and the green sheet may contain a butyral resin having a medium degree of polymerization.

The laminated body of the present invention is produced by the use of the foregoing ceramics paste. For example, the laminated body of the present invention may be produced by, if necessary, printing a predetermined circuit pattern with the foregoing ceramics paste on each green sheet, drying the pattern to evaporate the solvent and form ceramics layers, and pressure-bonding the green sheets with each other to stack the sheets. The laminated body may be subjected to cavity formation by punching or the like, as needed. In this case, the butyral resin contained in the green sheets is preferably different from that in the ceramics layers. For example, the ceramics paste may contain a butyral resin having a low degree of polymerization. The green sheets may contain a butyral resin having a medium degree of polymerization. This further facilitates inhibition of the sheet attack of the solvent in the ceramics paste against the green sheets.

Next, the laminated body which is produced by the use of the foregoing ceramics paste and a sensor element will be described. Here, a NOx sensor 100, which is a gas sensor, is described. The NOx sensor 100 includes a sensor element 110 configured to detect the concentration of NOx in a target gas measured and a heater portion 70 adjacent to the sensor element 110, as illustrated in the lower section of FIG. 1. The sensor element 110 has a structure in which six layers, i.e., a first substrate layer 1, a second substrate layer 2, a third substrate layer 3, a first solid-electrolyte layer 4, a spacer layer 5, and a second solid-electrolyte layer 6, which are oxygen ion-conducting solid electrolyte layers composed of, for example, zirconia ($ZrO_2$), are stacked, in that order, from the bottom in FIG. 1. The solid electrolyte constituting each of the six layers is dense. The heater portion 70 is formed between the second substrate layer 2 and the third substrate layer 3 and can adjust the temperature of the entire sensor element 110 to a temperature at which the solid electrolyte is activated by the heat generation of a resistance heating element 72. The structure and the operating principle of the NOx sensor 100 as described above are known (for example, see Japanese Unexamined Patent Application Publication No. 2008-164411).

The sensor element 110 is formed by stacking the first solid-electrolyte layer 4, the spacer layer 5, and the second solid-electrolyte layer 6. In the sensor element 110, a gas inlet 10, a first diffusion-controlling portion 11, a buffer space 12, a second diffusion-controlling portion 13, a first internal cavity 20, a third diffusion-controlling portion 30, and a second internal cavity 40 are formed, in that order, from an end (left end in FIG. 1) toward the inside and arranged between the lower surface of the second solid-electrolyte layer 6 and the upper surface of the first solid-electrolyte layer 4 so as to communicate with one another. The gas inlet 10, the buffer space 12, the first internal cavity 20, and the second internal cavity 40 are formed as spaces by hollowing the spacer layer 5 and located between the first solid-electrolyte layer 4 and the second solid-electrolyte layer 6. A reference gas introduction space 43 is formed as a space by hollowing the first solid-electrolyte layer 4 and located between the third substrate layer 3 and the spacer layer 5. For example, air is introduced into the reference gas introduction space 43 as a reference gas used in the measurement of the concentration of NOx. An air introduction layer 48 is provided between the first solid-electrolyte layer 4 and the third substrate layer 3. The reference gas is introduced into the air introduction layer 48 through the reference gas introduction space 43. A reference electrode 42 is formed between the upper surface of the third substrate layer 3 and the lower surface of the first solid-electrolyte layer 4. The air introduction layer 48 exposed to the reference gas introduction space 43 is provided around the reference electrode 42. Oxygen concentrations (oxygen partial pressure) in the first internal cavity 20 and the second internal cavity 40 can be measured with the reference electrode 42.

The first internal cavity 20 serves as a space to adjust oxygen partial pressure in a target gas introduced through the second diffusion-controlling portion 13. A main pump cell 21 includes an inner pump electrode 22 formed in the first internal cavity 20, an outer pump electrode 23 provided on a surface of the second solid-electrolyte layer 6 opposite the side on which the inner pump electrode 22 lies, and the second solid-electrolyte layer 6 interposed between these electrodes 22 and 23. The inner pump electrode 22 includes a top electrode portion 22a formed on the lower surface of the second solid-electrolyte layer 6 and a bottom electrode portion 22b formed on the upper surface of the first solid-electrolyte layer 4. The operation of the main pump cell 21 enables the adjustment of the oxygen partial pressure. The inner pump electrode 22, the second solid-electrolyte layer 6, the spacer layer 5, the first solid-electrolyte layer 4, the third substrate layer 3, and the reference electrode 42 constitutes an electrochemical sensor cell, i.e., an oxygen partial pressure-detecting sensor cell 80 configured to control the main pump. The oxygen concentration (oxygen partial pressure) in an atmosphere in the first internal cavity 20 can be detected with the oxygen partial pressure-detecting sensor cell 80 configured to control the main pump.

The second internal cavity 40 serves as a space to perform a process for measuring the concentration of NOx in the target gas introduced through the third diffusion-controlling portion 30 and to adjust an oxygen partial pressure with an auxiliary pump cell 50. The auxiliary pump cell 50 includes an auxiliary pump electrode 51 which is provided in the second internal cavity 40 and which is in the form of a tunnel, the outer pump electrode 23, and the second solid-electrolyte layer 6. An oxygen partial pressure-detecting sensor cell 81 configured to control the auxiliary pump includes the auxiliary pump electrode 51, the reference electrode 42, the second solid-electrolyte layer 6, the spacer layer 5, the first solid-electrolyte layer 4, and the third substrate layer 3 and can control an oxygen partial pressure in an atmosphere in the second internal cavity 40. A measurement pump cell 41 includes a measurement electrode 44, the outer pump electrode 23, the second solid-electrolyte layer 6, the spacer layer 5, and the first solid-electrolyte layer 4. The concentration of NOx in a target gas is measured with the measurement pump cell 41. The measurement electrode 44 is covered with a porous fourth diffusion-controlling portion 45 and also functions as a NOx reduction catalyst to reduce NOx present in an atmosphere in the second internal cavity 40. An oxygen partial pressure-detecting sensor cell 82 configured to control a measurement pump includes the second solid-electrolyte layer 6, the spacer layer 5, the first solid-electrolyte layer 4, the third substrate layer 3, the measurement electrode 44, and the reference electrode 42. This cell can detect an oxygen partial pressure around the measurement electrode 44 can be detected.

In the NOx sensor 100 having the foregoing structure, by operating the main pump cell 21 and the auxiliary pump cell 50, a target gas whose oxygen partial pressure is always maintained at a constant small value (a value that does not substantially affect the measurement of NOx) is introduced into the measurement pump cell 41. Oxygen is generated by the reduction of NOx substantially in proportion to the concentration of NOx in the target gas. The resulting oxygen is pumped out by the measurement pump cell 41 to allow a pump current to flow. On the basis of the pump current, the concentration of NOx in the target gas can be determined.

An example of a method for producing the sensor element 110 will be described below. As illustrated in FIG. 2, first, a ceramics paste to be applied onto green sheets is prepared (paste preparation step S100). The ceramics paste is prepared by mixing ceramic particles, a resin, a solvent, and one or more additives selected from additives of a first group having a first structure containing one or more selected from ether structures, urethane structures, hydroxy group-containing structures, ester structures, and acrylic structures and additives of a second group having any one or more structures of the additives of the first group and a second structure containing one or more selected from imidazoline structures, ethylenediamine structures, and amine structures. As the ceramic particles, $ZrO_2$ particles containing 4 mol % $Y_2O_3$, which serves as a stabilizer, may be used, $Al_2O_3$ may be used for a porous portion. As the additives, an additive of the first group containing at least one selected from high-molecular-weight copolymers containing functional groups with affinities for ceramic particles, block copolymers containing functional groups with affinities for the ceramic particles, and phenol ethoxylate may be used. Alternatively, an additive of the second group containing at least one selected from compounds having alkenylimidazoline structures and polyoxyalkylene condensates of ethynediamine may be used. The additives of the first group and the additives of the second group may be used separately or in combination as a mixture of two or more. The first substrate layer 1, the second substrate layer 2, the third substrate layer 3, the first solid-electrolyte layer 4, the spacer layer 5, and the second solid-electrolyte layer 6 can be stacked with the ceramics paste. The mixing of the raw materials may be performed with, for example, a pot mill, a ball mill, a bead mill, a trammel, a planetary mill, or an attritor.

Next, ceramic particles are formed into a tape to produce green sheets (green sheet formation step S110). The green sheets can be formed by, for example, mixing ceramic particles, an organic binder, and an organic solvent together and subjecting the mixture to tape casting. As the ceramic particles, the foregoing stabilized ZrO2 particles may be used. Here, green sheets corresponding to six layers are produced.

After patterns of an electrode, an insulating layer, a resistance heating element, and so forth are formed in response to each of the first substrate layer 1, the second substrate layer 2, the third substrate layer 3, the first solid-electrolyte layer 4, the spacer layer 5, and the second solid-electrolyte layer 6 for the sensor element 110, the ceramics paste is applied and dried (printing and drying step S120). Each of the patterns may be formed by a method, for example, screen printing or a doctor blade method. As a method for applying the ceramics paste onto the green sheets, a method, for example, screen printing, gravure printing, or a doctor blade method, may be employed. Subsequently, the first substrate layer 1, the second substrate layer 2, the third substrate layer 3, the first solid-electrolyte layer 4, the spacer layer 5, and the second solid-electrolyte layer 6, which have been printed and dried, for the sensor element 110 are integrally stacked to form the laminated body 90 (see the upper section in FIG. 1) (stacking step S130).

The resulting laminated body 90 includes a plurality of sensor elements 110. The laminated body 90 is cut into pieces each having a size of a NOx sensor (cutting step S140). In the case where the green sheet laminated body is divided into a large number of pieces, cutting may be made with a knife edge. In the case of cutting the laminated body, cutting with a straight tooth, cutting with an angular tooth, and cutting with a rotary knife are exemplified. The cutting step may be performed by any one of these cutting tools. Here, when the laminated body 90 is cut with the knife edge, there is a problem of how to reduce the roughness of a cut surface. In general, if the cut surface is rough at the time of cutting, it will become a starting point of cracking after firing and will become a big problem of product manufacturing. We have studied this point in detail and have found that portions that are easily roughened at the time of cutting are located at boundaries between a green sheet and an adhesive layer of the laminated body of the green sheets and in the vicinity of the boundaries (see below-mentioned FIG. 3). Hitherto, in order to reduce the roughness of the cut surface of the laminated body, a knife temperature, a knife feed rate, a knife depth at the time of cutting, the shape of the edge, such as a single edge or double edge, and so forth have been devised. In contrast, in the present invention, the addition of the additive to the ceramics paste serving as an adhesive used for adhesive portions of the laminated body results in a further reduction in the roughness of the cut surface in the cutting step.

The pieces into which the laminated body 90 has been cut are fired (firing step S150). A predetermined inspection is performed (inspection step S160), thereby completing this process. In the firing step, firing may be performed in an air atmosphere at 1400° C. In this way, the NOx sensor 100 can be produced.

The ceramics paste according to this embodiment as described above in detail provides an appropriate surface to further reduce the occurrence of a failure. The reason for this is unclear but is believed that when the laminated body produced by the use of the ceramics paste is cut, a functional group and so forth contained in any of the foregoing additives act to adjust the adhesion of a cut surface of the laminated body to a cutting edge to an appropriate state. It is thus speculated that, for example, the appropriate shape of the cut surface results in a further inhibition of the occurrence of cracking and so forth that can occur at the cut surface of the laminated body after cutting, thereby further reducing the occurrence of a failure.

The present invention is not limited to the foregoing embodiments. It will be obvious that various embodiments may be performed without departing from the technical scope of the invention.

For example, in the foregoing embodiments, the NOx sensor 100 is produced by the use of the ceramics paste. However, the present invention is not particularly limited thereto as long as the ceramics paste is used. For example, in place of the NOx sensor 100, a gas sensor configured to detect ammonia, a hydrocarbon, or the like may be produced. Alternatively, the present invention may be used for ceramics other than sensors.

EXAMPLES

Examples in which ceramics pastes and laminated bodies are specifically produced are described below.

Examples 1 to 12

Ceramic particles, a butyral resin, a solvent, additives, and a plasticizer were mixed together to prepare ceramics pastes. As the ceramic particles, stabilized $ZrO_2$ particles having an average particle size of 0.50 μm and containing 4 mol % Y, $SiO_2$ particles, and $Al_2O_3$ particles were used. As the butyral resin, a butyral resin having a low degree of polymerization was used. As the solvent, a dihydroterpineol/2-ethylhexyl acetate (7:3) mixed solvent was used. As the plasticizer, a phthalate with an ester moiety having 8 carbon atoms was used. With respect to 100 parts by mass of the stabilized $ZrO_2$ particles, 2.5 parts by mass of $SiO_2$ particles, 1.5 parts by mass of $Al_2O_3$ particles, 13.5 parts by mass of the butyral resin, 62.9 parts by mass of the solvent, 2.1 parts by mass of the additive, and 2.4 parts by mass of the plasticizer were mixed together to prepare the ceramics paste. As the additives, each of DISPERBYK-108, DISPERBYK-162, DISPERBYK-164, DISPERBYK-182, DISPERBYK-2050, DISPERBYK-2155, and DISPERBYK-2164, which were available from BYK Japan K.K., and ADEKA TOL PC-6, ADEKA TOL PC-8, ADEKA TOL PC-10, ADEKA TOL SP-12, and ADEKA NOL B-4001, which were available from ADEKA CORPORATION, was mixed to a corresponding one of the ceramics pastes. Each ceramics paste containing a corresponding one of the additives of the first group was applied onto green sheets so as to have thicknesses of 7 μm, 20 μm, and 80 μm, thereby forming laminated bodies as illustrated in FIG. 1. The laminated bodies were cut with a knife into pieces, followed by firing at 1400° C. The fired pieces were defined as those of Examples 1 to 12 using the additives of the first group (see Table 1 described below).

Examples 13 to 20

Furthermore, ceramics pastes were prepared using additives of the first group. Pieces were produced by the same process as that in Example 1, except that SN-Spers 70, SN-Wet 366, and SN-Dispersant 9228, which were available from SAN NOPCO LTD., and TEGO Dispers 610, TEGO Dispers 652, TEGO Dispers 670, TEGO Dispers 685, and TEGO Dispers 700, which were available from EVONIK INDUSTRIES, were used as the additives. The resulting pieces were defined as those of Examples 13 to 20 (see Table 1 described below).

Examples 21 to 24

Ceramics pastes were prepared using additives of the second group. Pieces were produced by the same process as that in Example 1, except that DISPERBYK-109, which was available from BYK Japan K.K., and ADEKA NOL TR-702, ADEKA NOL TR-704, and ADEKA PLURONIC TR-913R, which were available from ADEKA CORPORATION, were used as the additives. The resulting pieces were defined as those of Examples 21 to 24 (see Table 1 described below).

Examples 25 to 28

Furthermore, ceramics pastes were prepared using additives of the second group. Pieces were produced by the same process as that in Example 1, except that NOPCO 38-C, NOPCO-Wet 50, which were available from SAN NOPCO LTD., and TEGO Dispers 630 and TEGO Dispers 662C, which were available from EVONIK INDUSTRIES, were used as the additives. The resulting pieces were defined as those of Examples 25 to 28 (see Table 1 described below).

Comparative Examples 1 to 5

Ceramics pastes were prepared using additives of the third group. Pieces were produced by the same process as that in Example 1, except that DISPERBYK-101, DISPERBYK-106, DISPERBYK-140, DISPERBYK-145, and DISPERBYK-180, which were available from BYK Japan K.K., were used as the additives. The resulting pieces were defined as those of Comparative Examples 1 to 5 (see Table 1 described below).

Comparative Examples 6 to 11

Furthermore, ceramics pastes were prepared using additives of the third group. Pieces were produced by the same process as that in Example 1, except that SN-Spers, SN-Dispersant 5027, SN-Dispersant 5468, Nopcosant RFA, and SN-Dispersant 5020, which were available from SAN NOPCO LTD., and TEGO Dispers 710, which was available from EVONIK INDUSTRIES, were used as the additives. The resulting pieces were defined as those of Comparative Examples 6 to 11 (see Table 1 described below).

Comparative Example 12

A piece was produced by the same process as that in Example 1, except that no additive was added. The resulting piece was defined as that of Comparative Example 12.

(Surface Roughness)

Surface roughnesses of cut surfaces of the pieces of Examples 1 to 28 and Comparative Examples 1 to 12 were measured with a laser microscope (VK-9710, manufactured by KEYENCE CORPORATION). Here, the maximum height Rmax (μm) was used to indicate the surface roughness.

(Cracking Rate)

The cut surfaces of the pieces of Examples 1 to 28 and Comparative Examples 1 to 12 were observed with a microscope to check the presence or absence of a crack. In each of Examples 1 to 28 and Comparative Examples 1 to 12, 1000 pieces were produced. The rate of the occurrence of cracking in 1000 pieces was defined as the cracking rate (%).

(Experimental Results and Discussion)

Figure 3:
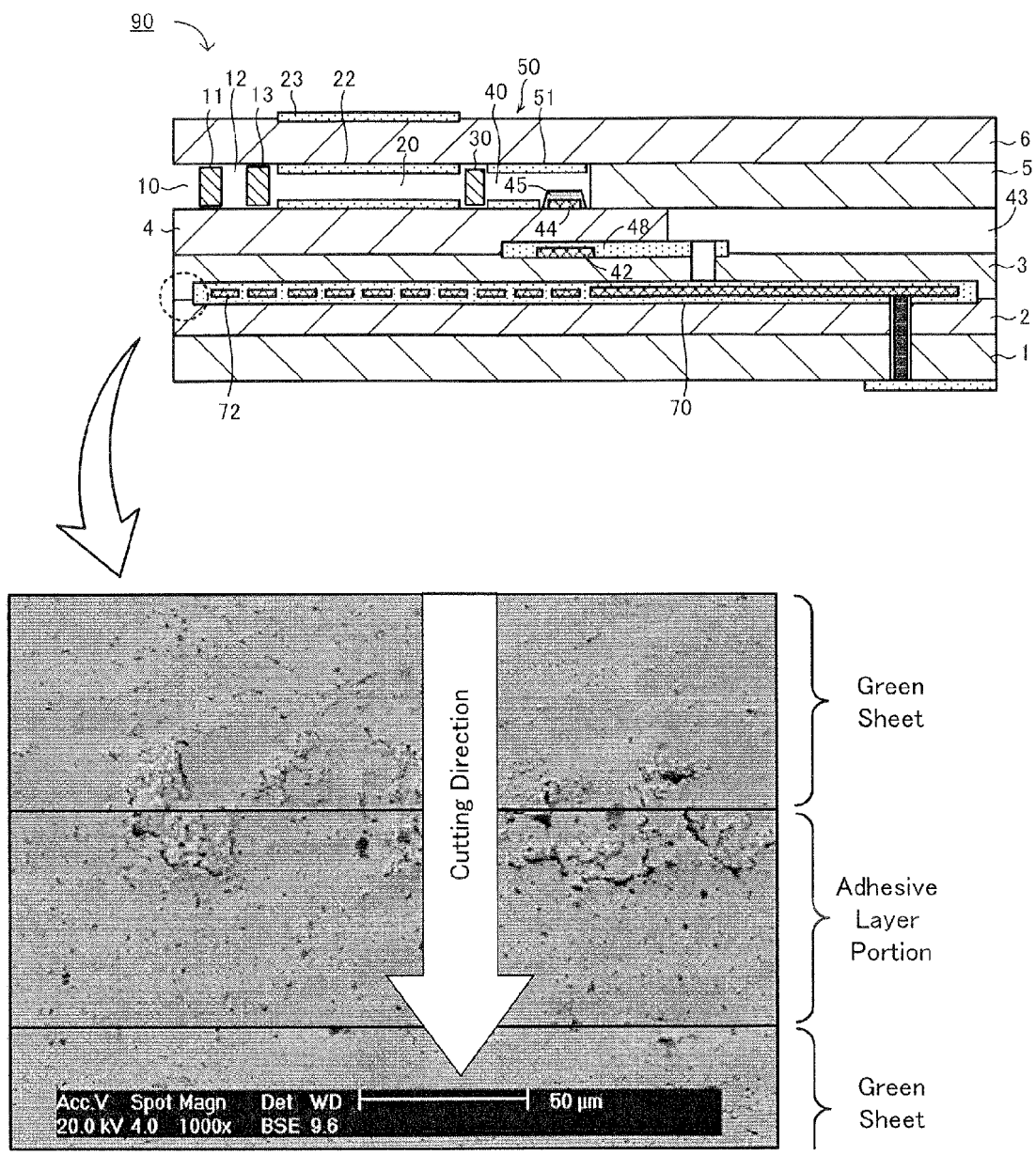
FIG. 3 is a photomicrograph of a section in Comparative Example 12, in which no additive is added.
Figure 4:
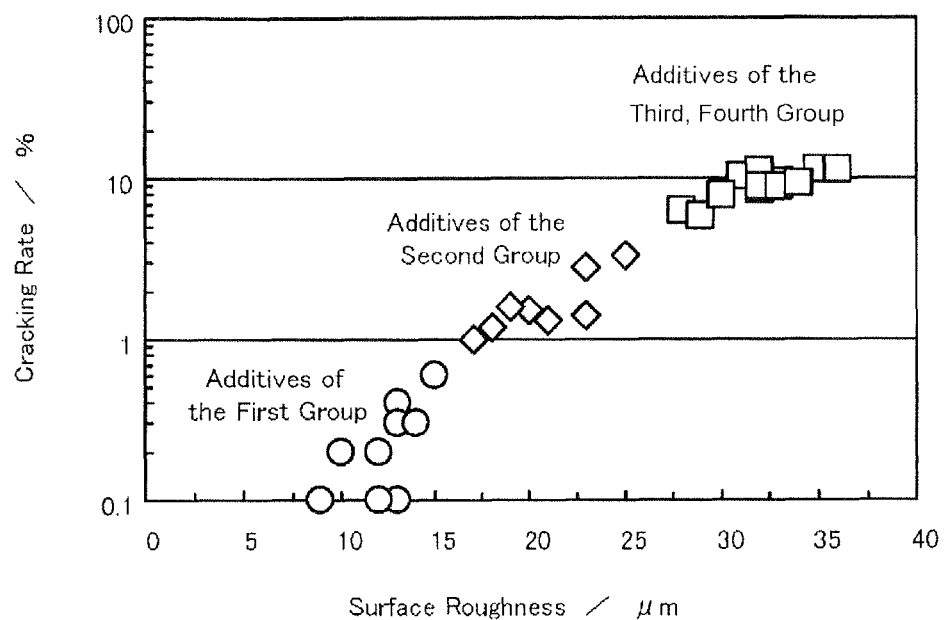
FIG. 4 is a graph illustrating the relationship of a cracking rate to the surface roughness.

Table 1 summarizes the measurement results. Table 1 describes the results when the ceramics pastes were applied onto the green sheets so as to have a thickness of 80 μm. The measurement results of samples applied so as to have thicknesses of 7 μm and 20 μm indicated the same tendency as in Table 1, so the description of the results was omitted. FIG. 3 is a photomicrograph of a cut surface in Comparative Example 12 in which no additive was added. FIG. 4 is a graph illustrating the relationship of a cracking rate to the surface roughness. Here, a phenomenon was observed in which when cutting was performed with a knife, an adhesive portion is dragged by the knife edge to cause a negative pressure in the dragged adhesive portion, and then the green sheet located on the outgoing knife side was drawn, so that the green sheet located on the outgoing knife side and the adhesive layer located on the incoming knife side were mechanically peeled off, because of a difference in adhesion to the knife edge between the green sheet portions and the adhesive layer portion composed of the ceramics paste in the laminated body due to their compositional structures (see FIG. 3). As described in Table 1, in each of Comparative Examples 1 to 11 in which a corresponding one of the additives of the third group was added and Comparative Example 12 in which no additive was added, each cut surface had a large surface roughness of 28 μm to 36 μm. In contrast, the addition of any one of the additives of the second group reduced the surface roughness to about 15 μm to about 25 μm. The addition of any one of the additives of the first group further reduced the surface roughness to about 5 μm to about 15 μm. The reason for this was presumably that, for example, the addition of the additive of the first group or second group allowed a polar portion of the resin in the adhesive layer to be capped, thereby reducing the chemical or physical adhesion (adherence) of the adhesive layer portion to the knife edge. This resulted in a reduction in the occurrence of the dragging phenomenon by the knife edge during cutting and a reduction in damage to the laminated body due to the dragging of the adhesive layer. As illustrated in FIG. 4, the cracking rate tended to decrease as the surface roughness decreased. As described above, the addition of the additive of the first group or second group to the ceramics paste results in the appropriate cut surface of the laminated body formed by the use of the ceramics paste to further reduce the occurrence of a failure, thereby achieving improvement in the yield of the element.

TABLE 1

| Group | | Additive | Surface Roughness (μm) | Cracking Rate (%) |
|---|---|---|---|---|
| First Group | Example 1 | DISPERBYK-108 | 10 | 0 |
| | Example 2 | DISPERBYK-162 | 8 | 0 |
| | Example 3 | DISPERBYK-164 | 9 | 0.1 |
| | Example 4 | DISPERBYK-182 | 9 | 0.1 |
| | Example 5 | DISPERBYK-2050 | 8 | 0 |
| | Example 6 | DISPERBYK-2155 | 12 | 0.2 |
| | Example 7 | DISPERBYK-2164 | 11 | 0 |
| | Example 8 | ADEKA TOL PC-6 | 13 | 0 |
| | Example 9 | ADEKA TOL PC-8 | 13 | 0.3 |
| | Example 10 | ADEKA TOL PC-10 | 12 | 0.1 |
| | Example 11 | ADEKA TOL SP-12 | 12 | 0.2 |
| | Example 12 | ADEKA NOL B-4001 | 13 | 0.1 |
| | Example 13 | SN-Spers 70 | 10 | 0 |

TABLE 1-continued

| Group | | Additive | Surface Roughness (μm) | Cracking Rate (%) |
|---|---|---|---|---|
| | Example 14 | SN-Wet 366 | 13 | 0.4 |
| | Example 15 | SN-Dispersant 9228 | 13 | 0.3 |
| | Example 16 | TEGO Dispers 610 | 12 | 0.2 |
| | Example 17 | TEGO Dispers 652 | 12 | 0.1 |
| | Example 18 | TEGO Dispers 670 | 10 | 0.2 |
| | Example 19 | TEGO Dispers 685 | 14 | 0.3 |
| | xample 20 | TEGO Dispers 700 | 15 | 0.6 |
| Second Group | Example 21 | DISPERBYK-109 | 18 | 1.2 |
| | Example 22 | ADEKA NOL TR-702 | 20 | 1.5 |
| | Example 23 | ADEKA NOL TR-704 | 23 | 1.4 |
| | Example 24 | ADEKA PLURONIC TR-913R | 21 | 1.3 |
| | Example 25 | NOPCO 38-C | 19 | 1.6 |
| | Example 26 | NOPCO-Wet 50 | 17 | 1 |
| | Example 27 | TEGO Dispers 630 | 25 | 3.3 |
| | Example 28 | TEGO Dispers 662C | 23 | 2.8 |
| Third Group | Comparative Example 1 | DISPERBYK-101 | 32 | 8.4 |
| | Comparative Example 2 | DISPERBYK-106 | 35 | 11.3 |
| | Comparative Example 3 | DISPERBYK-140 | 31 | 10.2 |
| | Comparative Example 4 | DISPERBYK-145 | 33 | 9.5 |
| | Comparative Example 5 | DISPERBYK-180 | 32 | 11 |
| | Comparative Example 6 | SN Spers | 28 | 6.3 |
| | Comparative Example 7 | SN-Dispersant 5027 | 36 | 11.2 |
| | Comparative Example 8 | SN-Dispersant 5468 | 32 | 8.8 |
| | Comparative Example 9 | Nopcosant RFA | 29 | 5.9 |
| | Comparative Example 10 | SN-Dispersant 5020 | 30 | 7.9 |
| | Comparative Example 11 | TEGO Dispers 710 | 33 | 8.8 |
| Fourth Group | Comparative Example 12 | No Additive | 34 | 9.3 |

INDUSTRIAL APPLICABILITY

The present invention can be used in the field of the production of a laminated body using a ceramics paste.

What is claimed is:

1. A ceramics adhesive comprising a paste including:
   ceramic particles,
   a resin capable of functioning as a binder of the ceramic particles,
   a solvent, and
   one or more additives selected from (i) additives of a first group having a first structure containing one or more selected from ether structures, urethane structures, hydroxy group-containing structures, ester structures, and acrylic structures, and (ii) additives of a second group having any one or more structures of the additives of the first group and having a second structure containing one or more selected from imidazoline structures, ethylenediamine structures, and amine structures,
   wherein the ceramics adhesive is used to bond green sheets for a gas sensor.

2. The ceramics adhesive according to claim 1, wherein each of the additives of the first group contain at least one selected from low-molecular-weight organic compounds containing functional groups with affinities for the ceramic particles, high-molecular-weight copolymers containing functional groups with affinities for the ceramic particles, block copolymers containing functional groups with affinities for the ceramic particles, oligomers containing functional groups with affinities for the ceramic particles, and phenol ethoxylate containing functional groups with affinities for the ceramic particles.

3. The ceramics adhesive according to claim 1, wherein each of the additives of the second group contain at least one selected from compounds having alkenylimidazoline structures and polyoxyalkylene condensates of ethylenediamine.

4. The ceramics adhesive according to claim 1, wherein the ceramic particles are one or more selected from alumina particles, silica particles, titania particles, zinc oxide particles, and zirconia particles.

5. A laminated body which is produced by the use of the foregoing ceramics adhesive according to claim 1.

6. The ceramics adhesive according to claim 1, wherein the resin capable of functioning as a binder of the ceramic particles is a butyral resin.

7. The ceramics adhesive according to claim 1, wherein the solvent is a mixture of two or more of 2-ethylhexanoic acid, 2-ethylhexanol, 2-ethylhexyl acetate, and 2-ethylhexyl methacrylate, α-terpineol, β-terpineol γ-terpineol and dihydroterpineol.

8. The ceramics adhesive according to claim 7, wherein the solvent is a mixture of 2-ethylhexyl acetate and dihydroterpineol.

9. A laminated body comprising a green sheet containing ceramic particles and, formed on the green sheet, the ceramics adhesive according to claim 1.

10. The laminated body according to claim 9, wherein the green sheet contains ceramic particles and a butyral resin.

11. The laminated body according to claim 10, wherein the resin present in the ceramics adhesive is a butyral resin which is different from the butyral resin present in the green sheet.

12. A method of making a laminated body for a gas sensor, comprising the steps of:
   (i) forming, on a green sheet containing ceramic particles, a layer of the ceramics adhesive according to claim 1;
   (ii) drying the ceramics adhesive to evaporate the solvent and form ceramics layers;
   (iii) bonding a plurality of the ceramics layers to form a stack; and
   (iv) cutting the stack to form a laminated body.

* * * * *